United States Patent [19]
Abromaitis et al.

[11] Patent Number: 4,803,052
[45] Date of Patent: Feb. 7, 1989

[54] CARBON MONOXIDE DETECTOR

[75] Inventors: Andre T. Abromaitis, Northbrook, Ill.; Marion A. Keyes, IV, Chagrin Falls, Ohio

[73] Assignee: The Babcock & Wilcox Company, New Orleans, La.

[21] Appl. No.: 729,889

[22] Filed: May 2, 1985

Related U.S. Application Data

[63] Continuation of Ser. No. 431,430, Sep. 30, 1982.

[51] Int. Cl.$^4$ .............................................. G01N 21/05
[52] U.S. Cl. ..................................... 422/91; 250/345; 356/410; 356/437; 422/93; 436/134
[58] Field of Search ................ 250/343, 345; 356/410, 356/411, 436, 437; 422/83, 90, 91, 93; 436/133, 134

[56] References Cited

U.S. PATENT DOCUMENTS

| Re. 31,438 | 11/1983 | Ueda | 250/345 |
| 2,019,871 | 11/1935 | Pettingill et al. | 356/411 X |
| 2,431,899 | 12/1947 | Wolf et al. | 422/83 X |
| 4,120,592 | 10/1978 | Fleming et al. | 250/343 X |
| 4,306,153 | 12/1981 | Fabinski et al. | 250/345 X |
| 4,371,785 | 2/1983 | Pedersen | 250/345 X |

FOREIGN PATENT DOCUMENTS

56-97868 8/1981 Japan ................... 436/134

OTHER PUBLICATIONS

Karels et al., Continuous Method for Sampling Stack Gases for Total Carbon, Environ. Sci. and Techn. 1978, pp. 1046-1051.

Primary Examiner—Michael S. Marcus
Attorney, Agent, or Firm—Vytas R. Matas; Robert J. Edwards

[57] ABSTRACT

A carbon monoxide detector comprises a single monochromatic infrared source which is arranged to alternately direct light through two separate gas-containing test chambers. The first chamber is supplied with gas to be tested which has an unknown carbon monoxide content. A catalytic burning chamber is connected between the first and second chambers to receive gas from the first chamber, burn the carbon monoxide in the gas to carbon dioxide and supply the carbon monoxide free gas to the second chamber. A single infrared light detector is provided for receiving light as it comes alternately from the two chambers. The light from the two chambers is compared to determine the amount of carbon monoxide present in the gas of the first test chamber. Since the same background gas is provided in both chambers and only a single infrared source and detector are utilized, inaccuracies due to differences in background detection, infrared source intensity and infrared detector sensitivity are overcome.

6 Claims, 1 Drawing Sheet

CARBON MONOXIDE DETECTOR

This is a continuation of application Ser. No. 431,430, filed Sept. 30, 1982, now abandoned.

FIELD AND BACKGROUND OF THE INVENTION

The present invention relates, in general, to gas-testing equipment and, in particular to a new and useful carbon monoxide detector.

Carbon monoxide (CO) is known to absorb infrared radiation. CO detectors have taken advantage of this phenomenon to determine the differences between infrared radiation absorption in a test cell containing a gas to be tested and a reference cell containing a fixed composition of gas, for example nitrogen. Since the background gas in the test and reference cells are different, inaccuracies may enter the detection operation.

The detection of carbon monoxide content is particularly important in flue gases generated in various industrial operations. One technique for detecting organic carbon as well as carbon monoxide in such industrial waste is disclosed in an article entitled "Continuous Method for Sampling Stack Gases for Total Carbon", G. G. Karels and R. C. Vincent, *Environmental Science and Technology*, Am. Chem. Soc., 1978, Vol. 12. This reference mentions various techniques for detecting carbon monoxide including the use of infrared analysis.

SUMMARY OF THE INVENTION

According to the invention, an improved CO detector is provided which utilizes a single monochromatic infrared source which produces infrared light that is absorbed by carbon monoxide molecules. In addition, a single infrared detector is utilized. Both source and detector are commutated between a measuring absorption tube and a reference absorbing tube to eliminate inaccuracies resulting from change in background concentrations. IR source intensity, or IR detector sensitivity.

Carbon monoxide containing gas such as flue gas is supplied to the measuring absorbing tube. The gas is then supplied through a catalytic chamber which converts carbon monoxide to carbon dioxide and then to the reference absorbing chamber. Since the flue gas itself is used as a reference gas, the interfering gases or background gases are the same for both tubes and therefore do not effect measurement accuracy.

Accordingly, an object of the present invention is to provide a CO detector which comprises a source of IR radiation, a measuring chamber for receiving a gas to be tested for CO, a reference chamber, a reaction chamber connected between the measuring and reference chambers for converting CO to $CO_2$ and for receiving gas from the measuring chamber and supplying it to the reference chamber, said reference and measuring chambers having IR transparent means defining a first and a second IR radiation path therethrough, respectively, beam splitting means associated with said IR source for directing IR radiation along said first and second paths, an IR detector for detecting IR radiation of said first and second paths after the IR radiation has passed through said measuring and radiation chambers respectively, and circuit means connected to said detector for determining the difference of IR radiation along said first and second paths after said measuring and reference chambers respectively which is a function of CO concentration in the gas of said measuring chamber.

A further object of the invention is to provide a reflector in each of said paths for reflecting IR radiation to a single detector.

A still further object of the invention is to provide a Pockel effect chopper in each IR transparent means for alternately supplying IR radiation to said first and second paths.

A still further object of the invention is to provide such a CO detector wherein the circuit means includes a log ratio circuit, the function being:

$$C_1 = A_1 + A_2 \ln \frac{I_{out\text{-}2}}{I_{out\text{-}1}}$$

wherein $C_1$ is equal to the CO concentration in the measuring tube, $A_1$ and $A_2$ are calibration constants and $I_{out\text{-}1}$ and $I_{out\text{-}2}$ are the amounts of IR radiation along the first and second paths.

A further object of the invention is to provide a carbon monoxide detector which is simple in design, rugged in construction and economical to manufacture.

For an understanding of the principles of the invention, reference is made to the following description of a typical embodiment thereof as illustrated in the accompanying drawing.

DESCRIPTION OF THE PREFERRED EMBODIMENT

Figure 1:
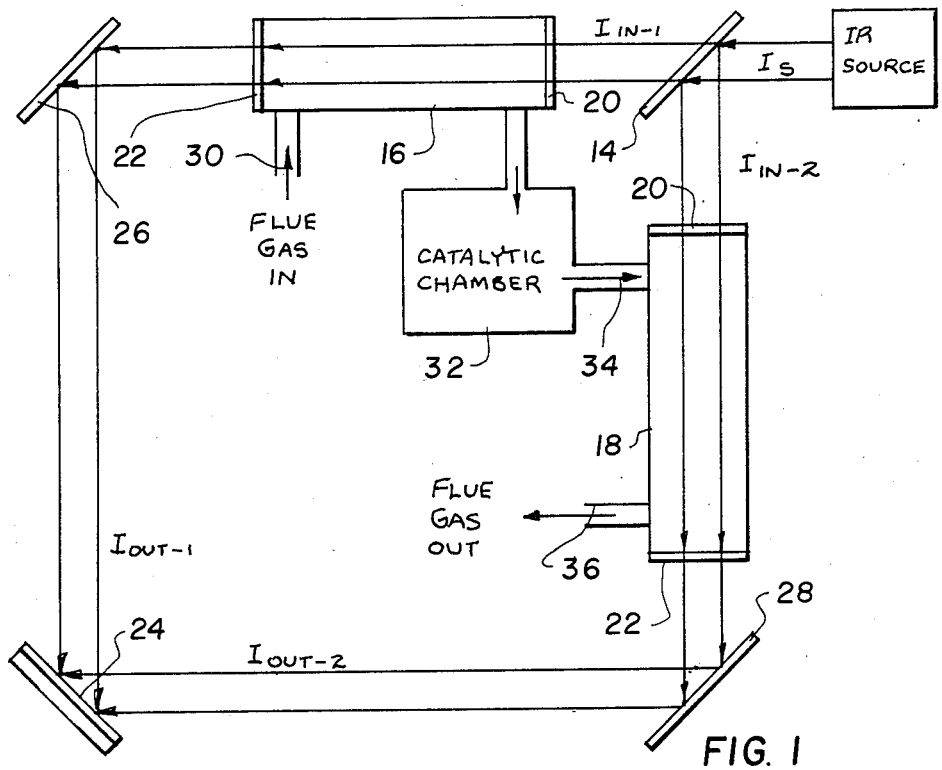
FIG. 1 is a diagram illustrating the carbon monoxide detector according to the invention.
Figure 2:
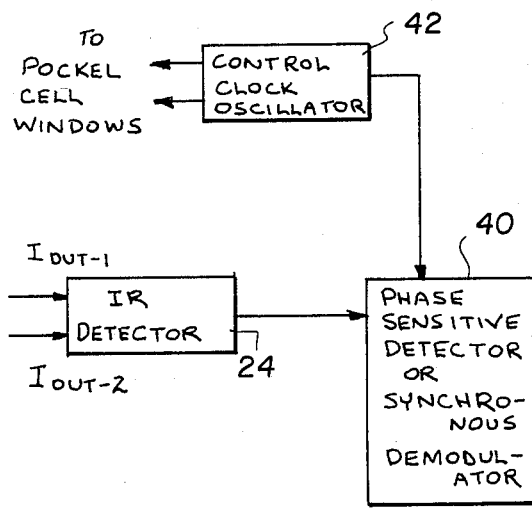
FIG. 2 is a block diagram illustrating exemplary circuitry useful in determining carbon monoxide concentrations according to the invention.

Referring to FIG. 1, an IR source 12 is provided which is a monochromatic source of infrared radiation that is significantly absorbed by CO. This source is used to generate an intensity of IR radiation $I_s$ which is separated into two components in $I_{IN\text{-}1}$ and $I_{IN\text{-}2}$ by a beam splitter 14. $I_{IN\text{-}1}$ and $I_{IN\text{-}2}$ are alternately passed through absorbing tubes 16, 18 by use of a Pockels effect chopper 20 in front of each tube, and an IR transparent window 22 at the opposite end of each tube. Intensities $I_{OUT\text{-}1}$ and $I_{OUT\text{-}2}$ are then directed to a common IR detector 24 by use of infared reflectors 26 and 28. $I_{OUT\text{-}1}$ and $I_{OUT\text{-}2}$ are then measured alternately by use of phase sensitive detector synchronized with the Pockels effect choppers (FIG. 2).

In operation, flue or other CO containing gas is supplied to the measuring tube 16 over inlet 30. The incoming flue gas must have sufficient available oxygen in it to convert all the CO to $CO_2$. This is usually available for low concentrations of CO. However, under some operating conditions, it may be desirable to add some ambient air with the incoming flue gas before it reaches the first absorbing tube 16. The gas then flows to a catalytic chamber 32 where all the CO is converted to $CO_2$ in known fashion. CO free gas with substantially the same background characteristic is then supplied to reference tube 18 over connection 34 and finally out of tube 18 over outlet 36.

According to Beer's Law:

$$I_{OUT-1} = K_1 I_s (e^{-\mu L_1(C_1+B_1)})$$

$$I_{OUT-2} = K_2 I_s (e^{-\mu L_2(C_2+B_2)})$$

Where:
$I_s$ = Source Intensity;
$K_1$ = Loss coefficient associated with the beam splitter, chopper, IR window, and reflector for a first path through tube 16 to detector 24;
$K_2$ = Loss coefficient associated with the beam splitter, chopper, IR window, and reflector for a second path through tube 18 to the detector;
$\mu$ = Extinction coefficient for the particular wavelength being used;
$L_1$ = Path Length through absorbing tube 16;
$L_2$ = Path Length through absorbing tube 18;
$C_1$ = CO concentration in absorbing tube 16;
$C_2$ = CO concentration in absorbing tube 18;
$B_1$ = Background gas concentration in absorbing tube 16; and
$B_2$ = Background gas concentration in absorbing tube 18.

$$\frac{I_{OUT-1}}{I_{OUT-2}} = \frac{K_1 I_s (e^{-\mu L_1(C_1+B_1)})}{K_2 I_s (e^{-\mu L_2(C_2+B_2)})} \tag{3}$$

$$= \frac{K_1}{K_2} \frac{(e^{-\mu L_1 C_1})(e^{-\mu L_1 B_1})}{(e^{-\mu L_2 C_2})(e^{-\mu L_2 B_2})} \tag{4}$$

And since $B_2 \cong B_1$ $\mu \triangleq \mu$ and $L_1 = L_2$ by mechanical construction of the instrument and $C_2 = 0$
Then:

$$\frac{I_{OUT-1}}{I_{OUT-2}} = \frac{K_1}{K_2} (e^{-\mu L C_1}) \tag{5}$$

Then:

$$\frac{K_2 I_{OUT-1}}{K_1 I_{OUT-2}} = e^{-\mu L C_1} \tag{6}$$

and $$\ln \frac{K_2 I_{OUT-1}}{K_1 I_{OUT-2}} = -\mu L C_1 \tag{7}$$

or:

$$C_1 = \frac{1}{\mu L} \ln \frac{K_1 I_{OUT-2}}{K_2 I_{OUT-1}} \tag{8}$$

$$= \frac{1}{\mu L} \ln \frac{K_1}{K_2} + \ln \frac{I_{OUT-2}}{I_{OUT-1}} \tag{9}$$

$$C_1 = A_1 + A_2 \ln \frac{I_{OUT-2}}{I_{OUT-1}} \tag{10}$$

Where $A_1$ and $A_2$ are treated as calibration constants in adjusting the gain and zero of the instrument.

Referring now to FIG. 2, the IR detector 24 which alternately receives infared radiation along the first and second paths supplies its signal to a phase sensitive detector or synchronous demodulator 40 which is controlled by a clock 42 that also functions to control Pockel cell windows 20, 20. Demodulator 40 generates voltages $E_1$ and $E_2$ which are applied to a log ratio module 44. Voltages $E_1$ and $E_2$ are proportional to the infrared radiation $I_{OUT-1}$ and $I_{OUT-2}$ respectively which travel along the first and second paths. The log module 44 generates an output voltage $E_O$ on line 46 which equals $\log E_2/E_1$. This quantity, in turn, is directly proportional to the carbon monoxide concentration $C_1$ and can be used to operate an indicator.

The Pockel effect described in *Reference Data for Radio Engineers*, Howard W. Sams and Company. The log module 44 can be of the type designated 4127 manufactured by the Burr-Brown Research Corporation of Tuscon, Ariz.

While a specific embodiment of the invention has been shown and described in detail to illustrate the application of the principles of the invention, it will be understood that the invention may be embodied otherwise without departing from such principles.

We claim:
1. A CO detector for determining the CO concentration in a continuous test gas stream containing interfering or background gases comprising;
   a single source of substantially monochromatic IR radiation;
   a measuring chamber adapted to continuously receive a gas to be tested for CO;
   a reaction chamber connected to said measuring chamber for continuously receiving gas from said measuring chamber and for converting substantially all CO in the sample stream to $CO_2$;
   a reference chamber connected to said reaction chamber for continuously receiving a gas from said reaction chamber to be tested for CO;
   said measuring and reference chambers having IR transparent means defining first and second IR radiation paths therethrough;
   beam splitting means associated with said IR source for directing IR radiation along said first and second paths;
   an IR detector for detecting IR radiation of said first and second paths after the IR radiation has passed through said measuring and reference chambers respectively; and
   circuit means connected to said detector for continuously determing a difference between the IR radiation of said first and second paths absorbed in said measuring and reference chambers which difference is a function of the CO concentration of gas supplied to said measuring chamber.

2. A CO detector according to claim 1, wherein said beam splitting means comprises a beam splitter for receiving IR radiation from said IR source and supplying half of the IR radiation to said measuring chamber and half of the IR radiation to said reference chamber.

3. A CO detector according to claim 1, including an IR reflector in each of said first and second paths for reflecting IR radiation to said IR detector.

4. A CO detector according to claim 1, wherein said reaction chamber comprises a catalytic chamber for catalytically converting CO to $CO_2$.

5. A CO detector according to claim 1, wherein said circuit means comprises circuit elements for establishing the CO concentration $C_1$ according to the following function:

$$C_1 + A_1 + A_2 \ln \frac{I_{OUT-2}}{I_{OUT-1}};$$

wherein $A_1$ and $A_2$ are calibration constants, $I_{OUT-2}$ is the IR radiation supplied to said detector from said second path and $I_{OUT-1}$ is the IR radiation supplied to said detector along said first path.

6. A CO detector according to claim 1, wherein each of said IR transparent means includes chopper means for transmitting IR radiation to said measuring and reference chamber respectively of sequentially different times.

* * * * *